United States Patent [19]

Chang et al.

[11] 4,388,461

[45] Jun. 14, 1983

[54] PROCESS FOR PRODUCING ALPHA-PICOLINE

[75] Inventors: Clarence D. Chang, Princeton; Patrick D. Perkins, Titusville, both of N.J.

[73] Assignee: Mobil Oil Corporation, New York, N.Y.

[21] Appl. No.: 384,360

[22] Filed: Jun. 2, 1982

Related U.S. Application Data

[63] Continuation of Ser. No. 326,258, Dec. 1, 1981, abandoned.

[51] Int. Cl.$^3$ .................. C07D 213/09; C07D 213/73
[52] U.S. Cl. .................................... 546/251; 546/250
[58] Field of Search ................................ 546/250, 251

[56] References Cited

U.S. PATENT DOCUMENTS

| | | | |
|---|---|---|---|
| 3,272,865 | 9/1966 | Barker | 260/581 |
| 3,384,667 | 5/1968 | Hamilton | 260/585 |
| 3,860,650 | 1/1975 | Becker | 260/570 |
| 4,082,805 | 4/1978 | Kaeding | 260/585 |
| 4,220,783 | 9/1980 | Chang | 546/251 |

FOREIGN PATENT DOCUMENTS 2516316 10/1976 Fed. Rep. of Germany .
49-29176 8/1974 Japan .

OTHER PUBLICATIONS

Chem. Abs. XX, 39423(g), (1978).
U.S. Ser. No. 252,487, 4/81, Chang.

*Primary Examiner*—Robert T. Bond
*Attorney, Agent, or Firm*—Charles A. Huggett; Charles J. Speciale; L. G. Wise

[57] ABSTRACT

Alpha-picoline is produced by the ammoniation of phenol over a zeolite having a silica:alumina ratio of at least 12 and a constraint index of 1 to 12. The preferred zeolite is ZSM-5. Aniline is produced as a co-product and the alpha-picoline may be separated by distillation or extraction.

14 Claims, No Drawings

PROCESS FOR PRODUCING ALPHA-PICOLINE

This is a continuation of application Ser. No. 326,258, filed Dec. 1, 1981, now abandoned.

FIELD OF THE INVENTION

This invention relates to a process for the production of alpha-picoline.

THE PRIOR ART

Alpha-picoline (2-methyl pyridine) is an important industrial material which is used as a solvent and as an intermediate in the production of various dyes and resins such as the ABS copolymers. It is currently made from acetaldehyde and ammonia with the beta and gamma picoline isomers and 2-methyl-5-ethylpyridine being obtained as by-products.

Methods for producing nitrogenous aromatic compounds have been known in the past. For example, the Halcon-Scientific Design process has been used for the production of aniline by the gas phase ammonolysis of phenol at high pressure in the presence of a catalyst such as silica-alumina, with a promoter to inhibit coke formation. The process is described in "Industrial Organic Chemistry" Weissermel and Arpe, Verlag Chemie (Weinheim, N.Y.) 1978, pp. 327-330. In another process described in U.S. Pat. No. 3,860,650, organic amines are obtained by the ammoniation of phenolic compounds in the presence of a alumina catalyst. U.S. Pat. No. 3,272,865 describes a process for preparing aminated benzenes by reacting ammonia or another aminating agent with phenol or a substituted phenol at high temperature over an oxide catalyst.

U.S. patent application Ser. No. 252,487, filed Apr. 8, 1981 by C. D. Chang and W. H. Lang discloses a process for converting phenol and phenolic-type compounds to aniline by reaction with ammonia or an amine over a zeolite catalyst of specified properties. The process produces aniline in good yields with high selectivity.

SUMMARY OF THE INVENTION

It has now been found that alpha-picoline and substituted alpha-picolines may be prepared by reacting phenolic compounds with ammonia or another amine over zeolite catalysts. The product stream contains both aniline and alpha-picoline but the two may be readily separated by a number of different methods. The selectivity of the reaction to the production of alpha-picoline may be increased by various measures.

DESCRIPTION OF PREFERRED EMBODIMENTS

Phenol or another phenolic commpound is passed over the zeolite catalyst in the presence of ammonia or an organic amine. Suitable phenolic compounds which may be used include cresol (o-, m- or p-isomers or mixtures of the isomers) and other substituted phenols in which the substituent may be, for example, alkyl or halogen. Phenol is, however, the preferred material.

The phenolic compound is reacted over the catalyst with ammonia or an organic amine such as the primary alkylamines e.g. methylamine, ethylamine, propylamine, n-butylamine, sec-butylamine and tert-butylamine. Secondary amines such as dimethylamine and diethylamine may also be used, as may tertiary amines such as trimethylamine.

The process may be carried out in the liquid or the vapor phase using either the reactants by themselves or in the presence of solvents such as benzene or other diluents. The reaction is typically carried out at a pressure from atmospheric pressure to about 250 atmospheres and at a temperature of from 200° to 650° C. The space velocity will normally be in the range of 0.5 to 50 LHSV although, as mentioned below, the space velocity and other reaction conditions may be varied in order to control the composition of the product mixture.

The reactants are passed over a zeolite catalyst to achieve the desired conversion. The zeolite catalysts used in the reaction comprise a three dimensional lattice of $SiO_4$ tetrahedra crosslinked by the sharing of oxygen atoms and which may optionally contain other atoms in the lattice, especially aluminum in the form of $AlO_4$ tetrahedra; the zeolite will also include a sufficient cationic complement to balance the negative charge on the lattice. The zeolites used in the present process have a silica:alumina ratio of at least 12 and preferably at least about 30.

An important characteristic of the zeolites used in the process is that they provide constrained access to, and egress from the intracrystalline free space by having a pore dimension greater than about 5 Angstroms and pore windows of about a size such as would be provided by 10-membered rings of oxygen atoms formed by the regular disposition of the tetrahedra making up the anionic framework of the zeolite, the oxygen atoms themselves being bonded to the silicon or aluminum atoms at the centers of the tetrahedra. The zeolites used in this process freely sorb normal hexane and have a pore dimension greater than about 5 Angstroms. They also have a structure which provides constrained access by larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render the zeolites ineffective.

Rather than attempt to judge from crystal structure whether or not a zeolite possesses the necessary constrained access, a simple determination of the "Constraint Index" may be made.

Zeolites which are useful in the present process have a Constraint Index from 1 to 12. Constraint Index values for some typical zeolites are as follows:

| Zeolite | Constraint Index |
| --- | --- |
| ZSM-5 | 8.3 |
| ZSM-11 | 8.7 |
| ZSM-12 | 2 |
| ZSM-38 | 3 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Erionite | 38 |
| Amorphous Silica-Alumina | 0.6 |

A complete description of the method by which the Constraint Index may be determined is given in U.S. Pat. No. 4,016,218 to which reference is made.

Specific zeolites which may be used in the present process include ZSM-5, ZSM-11, ZSM-12, ZSM-35 and ZSM-38 which are disclosed, respectively, in U.S. Pat. Nos. 3,702,886; 3,709,769; 3,832,449; 4,016,245 and 4,046,859. Reference is made to these patents for complete details of these zeolites and the preparation. Of them, ZSM-5 is preferred.

When the zeolites have been prepared in the presence of organic cations they are catalytically inactive, possibly because the intracrystalline free space is occupied by organic cations from the forming solution. They may be activated by heating in an inert atmosphere at 540° C. for one hour, for example, followed by base exchange with ammonium salts followed lby calcination at 540° C. in air. The presence of organic cations in the forming solution may not be absolutely essential to the formation of the zeolite; but it does appear to favor the formation of this special type of zeolite.

Some natural zeolites may sometimes be converted to zeolites of the desired type by various activation procedures and other treatments such as base exchange, steaming, alumina extraction and calcination.

The zeolites preferably have a crystal framework density, in the dry hydrogen form, not substantially below about 1.6 g. cm$^{-3}$. THe dry density for known structures may be calculated from the number of silicon plus aluminum atoms per 1000 cubic Angstroms, as given, e.g., on page 19 of the article on Zeolite Structure by W. M. Meier included in "Proceedings of the Conference on Molecular Sieves, London April 1967", published by the Society of Chemical Industry, London, 1968. Reference is made to this paper for a discussion of the crystal framework density. A further discussion of crystal framework density, together with values for some typical zeolites, is given in U.S. Pat. No. 4,016,218, to which reference is made.

When synthesized in the alkali metal form, the zeolite is conveniently converted to the hydrogen form, generally by intermediate formation of the ammonium form as a result of ammonium ion exchange and calcination of the ammonium form to yield the hydrogen form. It has been found that although the hydrogen form of the zeolite catalyzes the reaction successfully, the zeolite may also be partly in the alkali metal form although the selectivity to alpha-picoline is lower with the zeolite in this form.

It may be desirable to incorporate the zeolite in another material resistant to the temperature and other conditions employed in the process. Such matrix materials include synthetic or naturally occurring or in the form of gelatinous precipitates or gels including mixtures of silica and metal oxides. Naturally occurring clays can be composited with the zeolite and they may be used in the raw state as originally mined or initially subjected to calcination, acid treatment or chemical modification. Alternatively, the zeolite may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia or silica-magnesia-zirconia. The matrix may be in the form of a cogel. The relative proportions of zeolite component and inorganic oxide gel matrix may vary widely with the zeolite content typically ranging from 1 to 99 percent by weight and more usually in the range of 5 to 80 percent weight of the composite.

The selectivity of the reaction to the production of alpha-picoline may be improved by appropriate choice of reaction conditions or catalyst. Reduction of the space velocity of the phenolic compound tends to result in an increase in the selectivity to alpha-picoline while conversion of reactant remains essentially constant. The space velocity of the phenol is generally from 0.1 to 2.0, preferably 0.1 to 1 WHSV with the ammonia space velocity generally from 0.1 to 2.0, preferably 0.1 to 1 LHSV, for the highest selectivity to alpha-picoline. Suitable adjustment of the ratio of the phenolic compound to the ammonia or amine will vary the proportion of alpha-picoline in the product stream, the use of higher proportions of ammonia relative to the phenolic compound favoring the production of the alpha-picoline. Reactant ratio is $NH_3$/phenol usually from 0.2 to 5 preferably 1 to 3.5, by weight. Selectivity may also be improved by using a catalyst which has been severely calcined. Calcination temperatures above 400° C. and preferably above 500° C. are preferred for this purpose. Calcination is generally carried out in air although an inert atmosphere such as nitrogen may also be used. The calcination treatment will generally last at least one hour and usually will not last longer than 24 hours.

As previously mentioned, the selectivity to alpha-picoline is also improved by using the zeolite at least partly in the hydrogen form. The presence of metals e.g. hydrogenation components such as nickel, may lead to greater selectivities but in certain cases other by-products may also be produced, giving a product of lower purity. Other metals may be introduced by conventional ion exchange techniques. It has also been noted that selectivity to alpha-picoline is higher with the lower silica: alumina ratios. For example, better selectivity is obtained with a ratio of 70:1 than 1600:1. Silica-alumina ratios below about 500 and usually below 100 are therefore preferred.

The alpha-picoline may be separated from the product stream by a number of different physical or chemical methods. Distillation is a convenient and preferred method as the boiling point of alpha-picoline is 129.4° C. and that of aniline, the major component of the product stream is 184.4° C. Extraction techniques may also be employed, using solvents having different affinities for the different components of the product stream; water is a suitable solvent for this purpose as alpha-picoline is infinitely soluble in it whereas aniline has a solubility of only 3.6% at 18° C. Successive extractions may be used to obtain a product of requisite purity. Appropriate separation techniques may also be performed after the components of the product stream have been converted to derivatives; when separation has been completed the derivative may be converted back to the original material.

The process is notable for the high selectivity to the production of the alpha isomer of picoline; the beta and gamma isomers are completely absent. A further advantage is that the proportion of alpha-picoline in the product stream, relative to aniline, may be brought up to about 20%, the same proportion in which these materials are used industrially. The present process therefore provides a highly attractive synthetic procedure.

The invention is illustrated by the following Examples.

EXAMPLES 1-4

Samples of ZSM-5 zeolite catalysts having silica:alumina ratios of 70:1 and 1600:1 respectively were prepared by calcining the corresponding ammonium forms in air at 538° C. for ten hours. NaZSM-5 was prepared by cation exchange of the 70:1 HZSM-5 with an excess of 1N sodium nitrate solution, using two overnight exchanges at room temperature, each followed by a calcination in air at 538° C. for ten hours, after which a further exchange was made with 4N sodium nitrate solution at 100° C. for one hour, followed by a calcination at 538° C. for ten hours.

Phenol was reacted with ammonia in the presence of each of the three catalysts described above (70:1 HZSM-5; 1600:1 HZSM-5 and 70:1 NaZSM-5) in a reactor which consisted of a 9 mm. stainless steel tube filled with 6 cm$^3$ (2.7 g.) of catalyst which had been sized to $-10+30$ U.S. Standard (2.0-0.59 mm aperture). The phenol was fed as a solution in benzene containing 75.8 weight percent phenol; the ammonia was fed as a liquid. Nitrogen (100 GHSV) was used to maintain the reactor pressure of 2860 kPa. Reactor temperature was 510° C. The results are set out below.

| Example | 1 | 2 | 3 | 4 |
|---|---|---|---|---|
| Catalyst | ZSM-5 H-Form | ZSM-5 H-Form | ZSM-5 H-Form | ZSM-5, Partial Na Exchange |
| Alpha value | 192 | 192 | 4.1 | 6 |
| SiO$_2$:Al$_2$O$_3$ ratio | 70 | 70 | 1600 | 70 |
| WHSV phenol | 1.12 | 0.28 | .28 | .28 |
| WHSV ammonia | 1.66 | 1.66 | .42 | .42 |
| Ammonia/phenol mole ratio | 8.2 | — | 8.2 | 8.2 |
| Conversion of phenol, % | 96.3 | 96.9 | 92.1 | 97.8 |
| Selectivity, wt % | | | | |
| Aniline | 91.3 | 84.9 | 96.5 | 94.1 |
| alpha-picoline | 6.0 | 9.8 | 2.5 | 5.0 |
| Toluidines | 1.3 | 3.4 | 0.6 | 0.3 |
| Xylidines | 0.3 | 0.5 | 0.1 | trace |
| Diphenylamine | 0.2 | 0.1 | trace | — |
| Indole | 0.4 | 0.5 | 0.1 | 0.2 |
| Quinoline | trace | 0.6 | 0.3 | 0.3 |
| Carbazole | 0.1 | 0.1 | trace | — |
| Acridine | 0.4 | — | — | — |

The results above show that the relatively low silica (70:1 silica:alumina) zeolite provided the highest selectivity to alpha-picoline but that a number of by-products were formed in slightly larger quantities. Comparison of Examples 1 and 2 shows that production of alpha-picoline is favored by increasing the residence time of the phenol in the reactor.

The alpha-picoline may be separated by distillation.

EXAMPLES 5-7

HZSM-5 (silica-alumina ratio of 70:1) was prepared from NH ZSM-5 by calcination in air at 538° C. for ten hours, followed by one hour at 1000° C. to give a severely calcined sample of HZSM-5.

A sample of HZSM-5 containing 5 weight percent nickel was made by vacuum impregnation of 5.0 g. HZSM-5 with a solution of 1.18 g. nickel nitrate hexahydrate in 8 ml. water, followed by oven drying overnight at 110° C. and calcination at 300° C. for two hours. A sample of HZSM-5 containing 5 weight percent copper was made in the same way using 1.64 g. of hydrated cupric nitrate. The metal-containing catalysts were treated overnight in hydrogen (250 GHSV) at 400° C. (Ni-HZSM-5) and 250° C. (Cu-ZSM-5) prior to reaction.

| Example | 5 | 6 | 7 |
|---|---|---|---|
| Catalyst | HZSM-5 (Calcined at 1000° C.) | HZSM-5 + 5% Ni | HZSM-5 + 5% Cu |
| WHSV phenol | 0.28 | 1.12 | 1.12 |
| LHSV ammonia | 0.42 | 1.66 | 1.66 |
| GHSV N$_2$ | 100 | — | — |
| GHSV H$_2$ | — | 200 | 200 |
| Conversion of Phenol, % | 93.9 | 99.4 | 98.0 |
| Selectivity, wt. % | | | |
| Aniline | 81.9 | 84.3 | 90.0 |
| alpha-picoline | 17.5 | 8.6 | 6.0 |
| Toluidines | 0.1 | 2.8 | 2.0 |
| Xylidines | 0.1 | 0.5 | 1.2 |
| Diphenylamine | — | 0.1 | 0.1 |
| Indole | 0.1 | 0.4 | 0.4 |
| Quinoline | 0.2 | — | 0.1 |
| Carbazole | 0.1 | 0.1 | — |
| Acridine | — | — | — |
| Acetonitrile | — | 0.4 | — |
| Propionitrile | — | 0.3 | — |
| Pyridine | — | 2.6 | 0.5 |

The results above show that selectivity to alpha-picoline may be improved by the use of a severe calcination treatment (Example 5). Also, the metal-containing catalysts, although effective for the conversion, produce a number of by-products including pyridine, indicating that dealkylation of the alpha-picoline may occur.

We claim:

1. A method of making an alpha-picoline by contacting a phenolic compound with ammonia or an amine in the presence of a crystalline zeolite catalyst having a silica:alumina ratio of at least 12 and a Constraint Index of 1 to 12 and separating the alpha-picoline from the resulting product stream.

2. A method according to claim 1 in which the phenolic compound is phenol.

3. A method according to claim 2 in which phenol is contacted with ammonia.

4. A method according to claim 3 in which the zeolite has a silica:alumina ratio of 12 to 100.

5. A method according to claim 3 in which the zeolite is ZSM-5.

6. A method according to claim 3 in which the zeolite is ZSM-11.

7. A method according to claim 3 in which the zeolite is ZSM-12.

8. A method according to claim 3 in which the zeolite is ZSM-35.

9. A method according to claim 3 in which the zeolite is ZSM-38.

10. A method according to claim 1 in which the alpha-picoline is separated from the resulting product stream by distillation.

11. A catalytic process for making an alpha-picoline which comprises
contacting a phenol compound selected from lthe group consisting of phenol, alkyl-substituted phenols and halogen-substituted phenols with ammonia or an organic amine at a temperature of about 200° to 650° C. in the presence of a crystalline zeolite catalyst having a silica:alumina ratio of at least about 12 and a constraint index of about 1 to 12.

12. The process of claim 11 wherein phenol is contacted with ammonia in the presence of a ZSM-5 catalyst and alpha-picoline is separated from the resulting product.

13. The process of claim 12 wherein the catalyst consists essentially of HZSM-5 and the NH$_3$/phenol reactant ratio is about 0.2 to 5 by weight.

14. The process of claim 11 wherein the process is conducted at a phenolic weight hourly space velocity of about 0.1 to 2 and the alpha-picoline is separated from the resulting product stream by distillation.

* * * * *

UNITED STATES PATENT AND TRADEMARK OFFICE
CERTIFICATE OF CORRECTION

PATENT NO. : 4,388,461

DATED : June 14, 1983

INVENTOR(S) : Clarence D. Chang and Patrick D. Perkins

It is certified that error appears in the above—identified patent and that said Letters Patent is hereby corrected as shown below:

Column 1, line 55, "commpound" should read --compound--.

Column 3, line 17, "1by" should read --by--.

Column 3, line 27, "THe" should read --The--.

Column 4, line 18, "Reactant ratio is $NH_3$/phenol" should read --Reactant ratio $NH_3$/phenol is--.

Column 6, line 59, in Claim 11, "1the" should read --the--.

Signed and Sealed this

Sixth Day of September 1983

[SEAL]

Attest:

Attesting Officer

GERALD J. MOSSINGHOFF

Commissioner of Patents and Trademarks